United States Patent
Pacetti

(10) Patent No.: US 8,361,538 B2
(45) Date of Patent: Jan. 29, 2013

(54) METHODS FOR APPLYING AN APPLICATION MATERIAL TO AN IMPLANTABLE DEVICE

(75) Inventor: Stephen Pacetti, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 672 days.

(21) Appl. No.: 12/331,290

(22) Filed: Dec. 9, 2008

(65) Prior Publication Data

US 2009/0181159 A1    Jul. 16, 2009

Related U.S. Application Data

(60) Provisional application No. 61/015,126, filed on Dec. 19, 2007.

(51) Int. Cl.
*B05D 3/14* (2006.01)
(52) U.S. Cl. ...................... 427/2.24; 427/2.31
(58) Field of Classification Search .................. 427/2.31, 427/2.24
See application file for complete search history.

(56) References Cited

U.S. PATENT DOCUMENTS

| | | | |
|---|---|---|---|
| 2,072,303 A | 3/1937 | Herrmann et al. |
| 3,882,816 A | 5/1975 | Rooz et al. |
| 3,995,075 A | 11/1976 | Cernauskas et al. |
| 4,269,713 A | 5/1981 | Yamashita et al. |
| 4,323,524 A | 4/1982 | Snowden |
| 4,541,564 A | 9/1985 | Berger et al. |
| 4,560,374 A | 12/1985 | Hammerslag |
| 4,642,581 A | 2/1987 | Erickson |
| 4,733,665 A | 3/1988 | Palmaz |
| 4,800,882 A | 1/1989 | Gianturco |
| 4,839,055 A | 6/1989 | Ishizaki et al. |
| 4,865,879 A | 9/1989 | Finlay |
| 4,886,062 A | 12/1989 | Wiktor |
| 4,977,901 A | 12/1990 | Ofstead |
| 4,978,067 A | 12/1990 | Berger et al. |
| 5,112,457 A | 5/1992 | Marchant |
| 5,219,120 A | 6/1993 | Ehrenberg et al. |
| 5,328,471 A | 7/1994 | Slepian |
| 5,455,040 A | 10/1995 | Marchant |
| 5,464,650 A | 11/1995 | Berg et al. |
| 5,558,900 A | 9/1996 | Fan et al. |
| 5,578,073 A | 11/1996 | Haimovich et al. |
| 5,605,696 A | 2/1997 | Eury et al. |
| 5,628,730 A | 5/1997 | Shapland et al. |
| 5,667,767 A | 9/1997 | Greff et al. |
| 5,670,558 A | 9/1997 | Onishi et al. |
| 5,700,286 A | 12/1997 | Tartaglia et al. |
| 5,716,981 A | 2/1998 | Hunter et al. |
| 5,800,392 A | 9/1998 | Racchini |
| 5,824,049 A | 10/1998 | Ragheb et al. |
| 5,830,178 A | 11/1998 | Jones et al. |
| 5,837,313 A | 11/1998 | Ding et al. |
| 5,851,508 A | 12/1998 | Greff et al. |
| 5,858,746 A | 1/1999 | Hubbell et al. |
| 5,865,814 A | 2/1999 | Tuch |
| 5,873,904 A | 2/1999 | Ragheb et al. |
| 5,891,507 A | 4/1999 | Jayaraman |
| 5,971,954 A | 10/1999 | Conway et al. |
| 5,980,928 A | 11/1999 | Terry |
| 5,980,972 A | 11/1999 | Ding |
| 6,010,530 A | 1/2000 | Goicoechea |
| 6,015,541 A | 1/2000 | Greff et al. |
| 6,030,371 A | 2/2000 | Pursley |
| 6,042,875 A | 3/2000 | Ding et al. |
| 6,051,648 A | 4/2000 | Rhee et al. |
| 6,056,993 A | 5/2000 | Leidner et al. |
| 6,060,451 A | 5/2000 | DiMaio et al. |
| 6,080,488 A | 6/2000 | Hostettler et al. |
| 6,083,257 A | 7/2000 | Taylor et al. |
| 6,096,070 A | 8/2000 | Ragheb et al. |
| 6,099,562 A | 8/2000 | Ding et al. |
| 6,110,188 A | 8/2000 | Narciso, Jr. |
| 6,113,629 A | 9/2000 | Ken |
| 6,120,536 A | 9/2000 | Ding et al. |
| 6,120,904 A | 9/2000 | Hostettler et al. |
| 6,121,027 A | 9/2000 | Clapper et al. |
| 6,129,761 A | 10/2000 | Hubbell |
| 6,153,252 A | 11/2000 | Hossainy et al. |
| 6,156,373 A | 12/2000 | Zhong et al. |
| 6,165,212 A | 12/2000 | Dereume et al. |
| 6,306,176 B1 | 10/2001 | Whitbourne |
| 6,358,556 B1 | 3/2002 | Ding et al. |
| 6,358,567 B2 | 3/2002 | Pham et al. |
| 6,364,903 B2 | 4/2002 | Tseng et al. |
| 6,368,658 B1 | 4/2002 | Schwarz et al. |
| 6,395,326 B1 | 5/2002 | Castro et al. |
| 6,407,009 B1 | 6/2002 | You et al. |

(Continued)

FOREIGN PATENT DOCUMENTS

| DE | 1152920 | 8/1963 |
|---|---|---|
| EP | 0665023 | 8/1995 |

(Continued)

OTHER PUBLICATIONS

U.S. Appl. No. 61/015,126, filed Dec. 19, 2007, Pacetti.

(Continued)

*Primary Examiner* — Kriellion Sanders
(74) *Attorney, Agent, or Firm* — Workman Nydegger; Ron Devore

(57) ABSTRACT

Devices and methods for applying a coating to an implantable device are disclosed. A method for applying a coating to an implantable device is disclosed. The method includes positioning an implantable device relative to an ultrasonic material delivery apparatus. The ultrasonic material delivery apparatus includes an ultrasonic generator. At least one of the ultrasonic material delivery apparatus and the implantable device has a positive or negative electric charge. An application material is applied to the implantable device using the ultrasonic material delivery apparatus.

29 Claims, 7 Drawing Sheets

U.S. PATENT DOCUMENTS

| | | | |
|---|---|---|---|
| 6,426,145 | B1 | 7/2002 | Moroni |
| 6,503,954 | B1 | 1/2003 | Bhat et al. |
| 6,534,112 | B1 | 3/2003 | Bouchier et al. |
| 6,555,157 | B1 | 4/2003 | Hossainy et al. |
| 6,696,121 | B2 | 2/2004 | Jung, Jr. et al. |
| 6,818,247 | B1 | 11/2004 | Chen et al. |
| 6,861,088 | B2 | 3/2005 | Weber et al. |
| 7,504,125 | B1 | 3/2009 | Paacetti et al. |
| 7,951,428 | B2 | 5/2011 | Hoerr et al. |
| 8,007,858 | B2 | 8/2011 | Pacetti et al. |
| 2004/0062875 | A1 | 4/2004 | Chappa et al. |
| 2006/0198940 | A1 | 9/2006 | McMorrow |
| 2007/0128343 | A1 | 6/2007 | Chappa |
| 2007/0254091 | A1 | 11/2007 | Fredrickson et al. |
| 2009/0136556 | A1 | 5/2009 | Pacetti et al. |
| 2009/0181159 | A1 | 7/2009 | Pacetti |

FOREIGN PATENT DOCUMENTS

| | | |
|---|---|---|
| EP | 0970711 | 1/2000 |
| GB | 1455862 | 11/1976 |
| WO | WO 91/12846 | 9/1991 |
| WO | WO 97/45105 | 12/1997 |
| WO | WO 99/63981 | 12/1999 |
| WO | WO 00/02599 | 1/2000 |
| WO | WO 00/12147 | 3/2000 |
| WO | WO 00/64506 | 11/2000 |
| WO | WO 01/01890 | 1/2001 |
| WO | WO 01/45763 | 6/2001 |
| WO | WO 2005/065843 | 7/2005 |
| WO | WO 2007/089881 | 8/2007 |
| WO | WO 2009/085618 | 7/2009 |
| WO | WO 2009/085619 | 7/2009 |

OTHER PUBLICATIONS

U.S. Appl. No. 61/015,137, filed Dec. 19, 2007, Pacetti.
SONO-TEK Accu Mist—for Single Stent Coating Applications, Internet Citation, Retrieved from the Internet on Apr. 1, 2005.
SONO-TEK Accu Mist—for Single Stent Coating Applications, Internet Citation, Retrieved from the Internet on Feb. 9, 2007.
SONO-TEK Micro Mist—for Stent Coating, Internet Citation, Retrieved from the Internet on Feb. 9, 2007.
SONO-TEK Accu Mist for Stent Coating [online] XP002529453 Retrieved from Internet: URL:http://www.sono-tek.com/print.php?page=41> [retrieved on May 25, 2009] Product description of AccuMist ultrasonic spray nozzle for stent coating. The whole document.
Peter J. Tarcha et al. "The Application of Ink-Jet Technology for the Coating and Loading of Drug-Eluting Stents" Annals of Biomedical Engineering, Kluwer Academic Publishers-Plenum Publishers, NE, vol. 35, No. 10, Jul. 19, 2007 pp. 1791-1799, XP019522973.
U.S. Appl. No. 12/331,301, Aug. 17, 2011, Office Action.
U.S. Appl. No. 12/331,301, Apr. 4, 2012, Notice of Allowance.
U.S. Appl. No. 09/849,293, filed Jun. 27, 2001, Roorda et al.
U.S. Appl. No. 10/040,538, filed Dec. 28, 2001, Pacetti et al.
U.S. Appl. No. 12/363,538, filed Jan. 30, 2009, Pacetti et al.
Barath et al., *Low Dose of Antitumor Agents Prevents Smooth Muscle Cell Proliferation After Endothelial Injury*; JACC vol. 13, No. 2; Feb. 1989:252A (Abstract).
Dichek et al., *Seeding of Intravascular Stents With Genetically Engineered Endothelial Cells*, Circulation 1989; 1347-1353.
Forester et al., *A Paradigm for Restenosis Based on Cell Biology: Clues for the Development of New Preventive Therapies*; J. Am. Coll. Cardio. 1991; 17:758-769.
Matsumaru et al.; *Embolic Materials for Endovascular Treatment of Cerebral Lesions*; J. Biomatter Sci. Polymer Edn., vol. 8, No. 7 (1997) pp. 555-569.
Miyasaki et al., *Antitumor Effect of Implanted Ethylene-Vinyl Alcohol Copolymer Matrices Containing Anticancer Agents on Ehrlich Ascites Carcinoma and P388 Leukemia in Mice*; Chem. Pharm. Bull. 33(6) (1985) pp. 2490-2498.
Miyazawa et al., *Effects of Pemirolast and Tranilast on Intimal Thickening After Arterial Injury in the Rat*; J. Cardiovasc. Pharmacol. (1997) pp. 157-162.
Ohsawa et al., *Preventive Effects of an Antiallergic Drug, Pemirolast Potassium, on Restenosis After Percutaneous Transluminal Coronary Angioplasty*; American Heart Journal (1998) pp. 1081-1087.
Shigeno, *Prevention of Cerebrovascular Spasm by Bosentan, Novel Endothelin Receptor*; Chemical Abstract 125:212307 (1996).
U.S. Appl. No. 10/040,538, Mar. 4, 2004, Restriction Requirement.
U.S. Appl. No. 10/040,538, Sep. 30, 2004, Office Action.
U.S. Appl. No. 10/040,538, Jul. 5, 2005, Office Action.
U.S. Appl. No. 10/040,538, Apr. 19, 2006, Office Action.
U.S. Appl. No. 10/040,538, Jan. 5, 2007, Office Action.
U.S. Appl. No. 10/040,538, Jan. 2, 2009, Notice of Allowance.
U.S. Appl. No. 12/363,538, Aug. 21, 2009, Restriction Requirement.
U.S. Appl. No. 12/363,538, Dec. 3, 2009, Office Action.
U.S. Appl. No. 12/363,538, Jun. 7, 2010, Office Action.
U.S. Appl. No. 12/363,538, May 16, 2011, Notice of Allowance.
U.S. Appl. No. 12/363,538, Aug. 10, 2011, Issue Notification.
U.S. Appl. No. 09/894,293, filed Jun. 27, 2001, Roorda et al.

METHODS FOR APPLYING AN APPLICATION MATERIAL TO AN IMPLANTABLE DEVICE

CROSS-REFERENCE TO RELATED APPLICATIONS

This application claims the benefit of and priority to U.S. Provisional Patent Application No. 61/015,126, filed Dec. 19, 2007, and entitled "Methods For Applying An Application Material To An Implantable Device" which is incorporated herein by reference in its entirety. This application also incorporates U.S. Provisional Patent Application No. 61/015,137, filed Dec. 19, 2007, and entitled "Methods For Applying An Application Material To An Implantable Device", by reference in its entirety.

FIELD OF THE INVENTION

The present invention relates generally to medical devices, and more particularly to methods for applying an application material to an implantable device.

BACKGROUND OF THE INVENTION

Percutaneous transluminal coronary angioplasty (PTCA) is a procedure for treating heart disease. This procedure generally entails introducing a catheter assembly into the cardiovascular system of a patient via the brachial or femoral artery and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

While PTCA is widely used, it suffers generally from two unique problems. First, the blood vessel may suffer acute occlusion immediately after or within the initial hours after the dilation procedure. Such occlusion is referred to as "abrupt closure." Abrupt closure occurs in approximately five percent of cases in which PTCA is employed. The primary mechanisms of abrupt closures are believed to be elastic recoil, vasospasm, arterial dissection, and/or thrombosis. The second problem associated with this procedure is the re-narrowing of an artery after an initially successful angioplasty. This re-narrowing is referred to as "restenosis," which typically occurs within the first six months after angioplasty. Restenosis is believed to be due to, among other things, the proliferation and migration of cellular components from the arterial wall, as well as through geometric changes in the arterial wall referred to as "remodeling."

To reduce occlusion of the artery, and the development of thrombosis and/or restenosis, an expandable interventional device or prosthesis, one example of which includes a stent, may be implanted in the lumen to maintain the vascular patency. Additionally, to better effectuate the treatment of such vascular disease, it may be preferable to load an intraluminal device or prosthesis with one or more beneficial agents, such as antiproliferatives, for delivery to a lumen. One commonly applied technique for the local delivery of a drug is through the use of a polymeric carrier coated onto the surface of a stent, as disclosed in Berg et al., U.S. Pat. No. 5,464,650, the disclosure of which is incorporated herein by reference thereto. Such conventional methods and products generally have been considered satisfactory for their intended purpose.

However, implantable devices, such as stents may be difficult to coat without webbing, cobwebs, or other defects due to their generally intricate geometry. They may also be difficult to uniformly coat (i.e. on the ablumenal, luminal, and sidewall surfaces). Because of these challenges, many commercialized drug eluting stents are being coated by a spray process. However, spray coating may suffer generally from the following: reduced coating speed, reproducibility, and/or coating efficiency (i.e. the amount of material sprayed actually coating the device).

Accordingly, it may be desirable to provide methods for applying an application material to an implantable device.

BRIEF SUMMARY

Methods for applying an application material to an implantable device are disclosed. In one embodiment, a method for applying a coating to an implantable device is disclosed. The method includes positioning an implantable device relative to an ultrasonic material delivery apparatus. The ultrasonic material delivery apparatus includes an ultrasonic generator. At least one of the ultrasonic material delivery apparatus and the implantable device has a positive or negative electric charge. The method includes applying an application material to the implantable device using the ultrasonic material delivery apparatus.

In another embodiment, a method for applying a coating to an implantable device is disclosed. The method includes positioning an implantable device between a conductive member and an ultrasonic material delivery apparatus. The ultrasonic material delivery apparatus includes an ultrasonic generator. The conductive member has either a positive or a negative charge. The method includes applying an application material to the implantable device using the ultrasonic material delivery apparatus.

In another embodiment, a method for applying a coating to an implantable device is disclosed. The method includes positioning a stent between an ultrasonic material delivery apparatus and a grounded conductive member. The ultrasonic material delivery apparatus includes an ultrasonic generator. At least one of the ultrasonic material delivery apparatus and the stent has a positive or negative electric charge. The method includes applying ultrasonic energy to an application material using the ultrasonic generator. The method also includes applying the application material to the stent using the ultrasonic material delivery apparatus.

In a further embodiment, a method for applying a coating to an implantable device is disclosed. The method includes positioning a conductive member between a stent and an ultrasonic material delivery apparatus. The ultrasonic material delivery apparatus includes an ultrasonic generator. The conductive member has a positive or a negative charge. The method includes applying ultrasonic energy to an application material using the ultrasonic generator. The method also includes applying the application material to the stent using the ultrasonic material delivery apparatus.

In some embodiments, the ultrasonic material delivery device includes a material delivery device. At least one of the material delivery device and the implantable device has a positive or negative electric charge. The material delivery device, in further embodiments, is selectively electrically isolated from the ultrasonic generator. The material delivery apparatus, in still further embodiments, combines ultrasonic atomization with a flowing gas stream.

The ultrasonic material delivery apparatus, in some embodiments, has a positive or negative electric charge and the positive or negative electric charge is of sufficient strength to facilitate atomization of the application material.

The implantable device, in some embodiments, is positioned between the ultrasonic material delivery apparatus and a conductive member. The conductive member, in further embodiments, has a positive or a negative charge or is grounded.

The conductive member, in some embodiments, is positioned between the implantable device and the ultrasonic material delivery apparatus. The conductive member, in further embodiments, has a positive or a negative charge. In still further embodiments, the conductive member is an annular shaped ring.

In some embodiments, the implantable device, the ultrasonic material delivery apparatus, or the conductive member has a difference in electrical potential of less than or equal to about 100 kV in either a positive or negative polarity. Both the implantable device and the ultrasonic material delivery apparatus, in further embodiments, have either a positive or a negative charge.

Applying the application material to the implantable device using the ultrasonic material delivery apparatus, in some embodiments, includes applying ultrasonic energy to the application material using the ultrasonic generator. In further embodiments, the applied ultrasonic energy is sufficient to facilitate atomization of the application material.

The application material, in some embodiments, includes a radiopaque material, at least one bioactive agent that is an anti-proliferative, anti-inflammatory, antineoplastic, anti-platelet, anti-coagulant, anti-fibrin, antithrombonic, antimitotic, antibiotic, antiallergic or antioxidant drug, a durable and/or biodegradable polymer, and/or a solvent. The implantable device, in further embodiments, is a closure element and/or a stent.

It is to be understood that both the foregoing general description and the following detailed description are exemplary and are intended to provide further explanation of the invention claimed.

The accompanying Figures, which are incorporated in and constitute part of this specification, are included to illustrate and provide a further understanding of the method and system of the invention. Together with the description, the Figures serve to explain the principles of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings.

Figure 1:
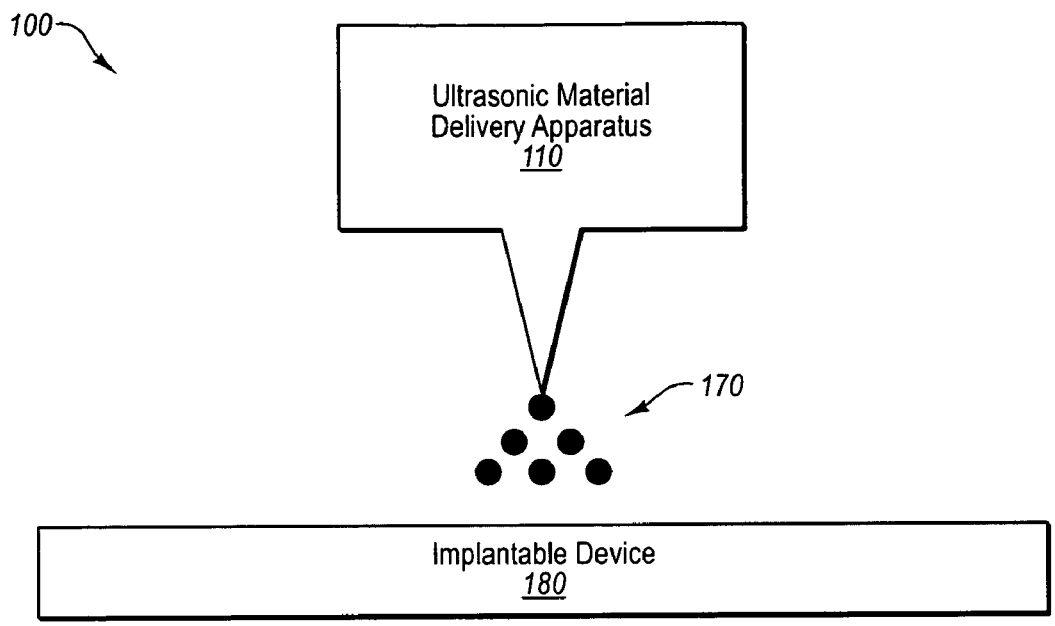
FIG. 1 illustrates a block diagram of an embodiment of a system for applying an application material to an implantable device, in accordance with the present invention.

It should be noted that the figures are not drawn to scale and that elements of similar structures or functions are generally represented by like reference numerals for illustrative purposes throughout the figures. It also should be noted that the figures are only intended to facilitate the description of embodiments of the present invention.

DETAILED DESCRIPTION

In one embodiment, a coating nozzle for an implantable device, such as a stent, is disclosed. The coating solution may be atomized by a combination of ultrasonic energy and application of an electric field. The ultrasonic energy is present to atomize the solution while the electrical field is applied to the nozzle primarily to impart an electric charge to the droplets so that they are attracted to a grounded part to be coated. However, if the applied electric field is high enough, it may also facilitate in the atomization.

Other embodiments include applying an electrical field to an ultrasonic material delivery apparatus, an implantable device, and/or a conductive member. In some embodiments, the implantable device may be placed between the ultrasonic delivery apparatus and the conductive member. In other embodiments, the conductive member may be placed between the ultrasonic delivery apparatus and the implantable device. The conductive member may be a single electrode, several electrodes that are interconnected, and/or a shaped electrode, such as a tubular, cylindrical, spherical, rectangular, and/or otherwise shaped electrode.

Further embodiments include grounding no more than two of the ultrasonic material delivery apparatus, the implantable device, and/or the conductive member. Still further embodiments include grounding either the ultrasonic material delivery apparatus or the implantable device. By setting up an electric field between the ultrasonic material delivery apparatus and the implantable device, the application material may generally follow a curved trajectory towards the implantable device, thereby generally increasing the coating efficiency.

Increased coating efficiency may be achieved by setting up an electric field between the ultrasonic material delivery apparatus and the conductive member and positioning the implantable device between the ultrasonic delivery apparatus and the conductive member. Due to the position of the conductive member, the application material may generally follow a curved trajectory towards the implantable device, thereby generally increasing the coating efficiency. In another embodiment, a focusing of application material droplets towards the implantable device may be achieved rather than attracting the droplets to the implantable device. Focusing the application material droplets may be achieved by positioning the conductive member between the ultrasonic delivery apparatus and the implantable device, and applying an electrical potential of the same sign to both the conductive member and the ultrasonic delivery apparatus. Use of a properly designed and positioned conductive member may repel application material droplets that are not on a trajectory toward the implantable device, and redirect them on a trajectory towards the implantable device.

These results, whether individually or collectively, can be achieved, according to one embodiment of the present invention, by employing methods, systems, and/or apparatus as shown in the figures and described in detail below.

Turning now to the drawings, FIG. 1 illustrates a block diagram of an embodiment of a system 100 for applying an application material 170 to an implantable device 180, in accordance with the present invention. The system 100 includes an ultrasonic material delivery apparatus 110 that may apply an application material 170 to an implantable device 180. The application material 170 may include beneficial agents, imaging materials, solvents, and/or other application materials.

Beneficial agents may include analgesics, antipyretics, antiasthmatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, antianginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, or combinations thereof. Preferably, the active agent includes at least one of rapamycin, rapamycin analog, sirolimus, everolimus, zotarolimus, 40-epi-(N1-tetrazolyl)-rapamycin, 40-O-[2-(2-hydroxy) ethoxy]ethyl-rapamycin, Biolimus A9 (Biosensors International, Singapore), deforolimus, AP23572 (Ariad Pharmaceuticals), temsirolimus, novolimus, myolimus, dexamethasone, dexamethasone acetate, dexmethasone phosphate, momentasone, cortisone, cortisone acetate, hydrocortisone, prednisone, prednisone acetate, betamethasone, betamethasone acetate, estradiol, acetaminophen, ibuprofen, naproxen, sulidac, heparin, taxol, paclitaxel, and/or combinations thereof.

Imaging materials may include materials, such as radiopaque materials. Examples of radiopaque materials may include high-density materials such as gold, platinum, platinum/iridium, tantalum, tungsten, gadolinium salts, gadolinium complexes, bismuth compounds, barium compounds, and/or other radiopaque materials. As used herein, the term radiopaque may include partial radiopacity as well as total radiopacity.

Solvents may include methanol, ethanol isopropanol, n-propanol, isobutanol, sec-butanol, n-butanol, benzyl alcohol, alcohols, diethyl ether, tetrahydrofuran, 1,4-dioxane, ethers, butyl acetate, isopropyl acetate, ethyl acetate, methyl acetate, esters, acetone, 4-butanone, cyclopentanone, cyclohexanone, ketones, 1-methoxy-2-propanol, diacetone alcohol, methylene chloride, chloroform, carbon tetrachloride, 1,1,1-trichloroethane, trichloroethylene, chlorobenzene, freons, pentane, hexane, cyclohexane, n-heptane, n-octane, benzene, toluene, o-xylene, p-xylene, m-xylene, dimethylenformamide, formamide, dimethylacetamide, dimethylsulfoxide, sulfolane, hexamethyl phosphorustriamide, n-methylpyrrolidone, 1,1,1-trifluoroethanol, hexafluoroisopropanol, water, and/or other solvents.

Other application materials may include polymeric materials comprised of phosphorylcholines, phosphorylcholine linked macromolecules, polyolefins, poly(meth)acrylates, polyurethanes, polyesters, polyanhydrides, polyphosphazenes, polyacrylates, acrylic polymers, poly(lactide-co-glycolides) (PLGA), polylactic acids (PLA), poly(hydroxybutyrates), poly(hydroxybutyrate-co-valerates), polydioxanones (PDO), polyorthoesters, polyglycolic acids (PGA), polycaprolactones (PCL), poly(glycolic acid-co-trimethylene carbonates), polyphosphoesters, polyphosphoester urethanes, poly(amino acids), cyanoacrylates, poly(trimethylene carbonate), poly(iminocarbonate), polyalkylene oxalates, polyiminocarbonates, aliphatic polycarbonates, fibrins, fibrinogens, celluloses, starchs, collagens, polycarbonate urethanes, polyisoprenes, polyisobutylenes, polybutadienes, polyethylenes, plasticized polyethylene terephthalates, polyethylene terepthalates, polymethylmethacrylates, poly(ethylene-co-ethylacrylates), poly(ethyl hexylacrylates), plasticized poly(ethylene-co-vinylacetates, polyvinyl acetates, poly(ethylene-co-vinyl acetates), poly(ethylene-co-vinyl alcohols), polyvinyl alcohols, cross-linked polyvinyl alcohols, cross-linked polyvinyl butyrates, polyvinylbutyrates, polybutylmethacrylates, polyvinyl chlorides, polyvinyl fluorides, polyvinylidene fluorides, poly(vinylidene fluoride-co-hexafluoropropylene), poly(vinylidene fluoride-co-chlorotrifluoroethylene), ethylene vinylchloride copolymers, silicones, polysiloxanes, substituted polysiloxanes, polyethylene oxides, polyethylene glycols (PEG), polybutylene terepthalate-co-PEG, PCL-co-PEG, PLA-co-PEG, polyvinyl acetals, polyvinyl acetates, polyamides, polyvinyl pyrrolidones, polyacrylamides, polyvinyl esters, copolymers thereof, polymer derivatives thereof, and/or combinations thereof.

Implantable devices 180 may include endoprostheses, drug delivery stents, drug delivery catheters, stent-grafts, grafts, drug delivery balloons, guidewires, orthopedic implants, PFO closure devices, pacemaker leads, dental implants, fixation screws, indwelling catheters, ocular implants, pharmacotherapeutic implants, blood-contacting components of extracorporeal devices, staples, filters, needles, tubes, coils, wires, clips, screws, sensors, plates, conduits, portions thereof, closure elements for engaging tissue, combinations thereof, and/or other implantable devices.

In one embodiment, the implantable device may include an endoprosthesis for controlling the release of an active agent therefrom. Such an endoprosthesis can include the following: a supporting metal structure configured and dimensioned to be used within a body of a human; a porous body disposed on and at least partially covering the supporting metal structure, said porous body including a first biocompatible material having a plurality of pores; a therapeutically effective amount of an active agent disposed within said pores, said therapeutically effective amount of the active agent being capable of treating and/or preventing a disease; an elution rate controlling matrix disposed within the porous body so as to contain said active agent within said pores, said matrix material including a polymeric biocompatible material that at least partially controls an elution rate of the active agent from the pores; and said pores each having a dimension that is configured to at least partially determine said elution rate.

In one embodiment, the implantable device may include a stent for controlling the release of an active agent therefrom. Such a stent can include the following: a superelastic metal structure configured and dimensioned as a stent to be used within a lumen of an animal; a porous body disposed on and at least partially covering the superelastic metal structure, said porous body including a first biocompatible material having a plurality of pores; a therapeutically effective amount of an active agent disposed within at least a portion of the pores, said therapeutically effective amount of the active agent being capable of treating and/or preventing a disease; and an elution rate controlling matrix disposed on at least one surface of the porous body so as to contain the active agent within said at least a portion of the pores, said matrix material including a second biocompatible material that controls an elution rate of the active agent from the pores. Optionally, the porous body is integrated with the supporting structure.

In another embodiment, the implantable device may include an endoprosthesis for controlling the release of an active agent therefrom. Such an endoprosthesis may include a supporting metal structure configured and dimensioned to be used within a body of a human, a coating body disposed on and at least partially covering the supporting metal structure, the coating body including a first biocompatible polymeric material having a largely homogeneous structure, a therapeutically effective amount of an active agent combined with the biocompatible polymeric material to make a largely homogeneous composition, the therapeutically effective amount of the active agent being capable of treating and/or preventing a disease, and the biocompatible polymeric material being either a durable or a biodegradable polymer.

In the present embodiment, the ultrasonic material delivery apparatus 110 and/or the implantable device 180 may have a positive or negative electric charge when applying the application material 170. Having an electric charge may include having an electric charge (i.e. positive, negative, or zero) with respect to a reference point. A reference point may include, for example, a ground. In some embodiments, the electric charge may be directly applied to a component by applying a voltage potential to the component while applying the application material 170. In further embodiments, a component may be grounded before and/or during the application of the application material 170. Grounding a component may include, for example, putting the component in electrical communication with a ground.

Typically, if the ultrasonic material delivery apparatus 110 has an electric charge, the application material 170 may have the same electric charge as the ultrasonic material delivery apparatus 110. For example, if the ultrasonic material delivery apparatus 110 has a positive electric charge the application material may also have a positive electric charge.

In embodiments where the application material 170 has an electric charge, the application material 170 may be generally attracted to or generally repelled from the implantable device 180. In some embodiments, the voltage potential between the application material 170 and the implantable device 180 may be sufficiently large to facilitate atomization of the application material 170.

In one example, the ultrasonic material delivery apparatus 110 may have a positive electric charge and the implantable device 180 may have a negative electric charge. When the ultrasonic material delivery apparatus 110 applies the application material 170 to the implantable device 180, the application material 170 may have a positive charge. The positively charged application material 170, in this example, may be generally attracted to the negatively charged implantable device 180.

In embodiments where the electric charge of the implantable device 180 is generally opposite the electric charge of the ultrasonic material delivery apparatus 110, the application material 170 may be generally more attracted to the implantable device 180 than in embodiments where only the ultrasonic material delivery apparatus 110 or the implantable device 180 have an electric charge. In embodiments where the electric charge of the implantable device 180 is generally opposite the electric charge of the ultrasonic material delivery apparatus 110 and where the opposite electric charges are relatively large, the application material 170 may be generally more attracted to the implantable device 180 than where the opposite electric charges are relatively small.

In another example, the ultrasonic material delivery apparatus 110 may have the same or similar electric charge as the implantable device 180 (i.e. both generally positive or both generally negative). When the ultrasonic material delivery apparatus 110 applies the application material 170 to the implantable device 180, the application material 170 may have the same or similar electric charge as the implantable device 180. The application material 170, in this example, may be generally repelled from the same or similarly charged implantable device 180. In embodiments where the electric charge of the implantable device 180 is generally similar to the electric charge of the ultrasonic material delivery apparatus 110 and where the similar electric charges are relatively large, the application material 170 may be generally more repelled by the implantable device 180 than where the similar electric charges are relatively small.

Repelling the application material 170 may be useful when it is desired to only apply the application material 170 to a surface closest to the ultrasonic material delivery apparatus 110 (i.e. the abluminal surface of a stent). For example, the application material 170 may have a velocity that is sufficient to overcome any repulsing force from the opposing electric charges and apply the application material 170 to a surface closest to the ultrasonic material delivery apparatus 110, but the velocity may be insufficient to overcome the repulsing force from the opposing electric charges to apply the application material 170 to another surface (i.e. the luminal surface of a stent).

In some embodiments, the ultrasonic material delivery apparatus 110 or the implantable device 180 may have an electric charge while the other device may be grounded. For example, if the ultrasonic material delivery apparatus 110 has an electric charge and the implantable device 180 is grounded, when the ultrasonic material delivery apparatus 110 applies the application material 170 to the implantable device 180, the application material 170 may be more attracted to the grounded implantable device 180 than to an implantable device that is not grounded. In another example, if the ultrasonic material delivery apparatus 110 is grounded and the implantable device 180 has an electric charge, when the ultrasonic material delivery apparatus 110 applies the application material 170 to the implantable device 180, the application material 170 (which may not have an electric charge because the ultrasonic material delivery apparatus 110 is grounded) may be more attracted to the charged implantable device 180 than to an implantable device that is not electrically charged.

FIG. 2 illustrates an embodiment of a method 200 for applying an application material to an implantable device, in accordance with the present invention. In the present embodiment, the method 200 may be used in conjunction with components of the system 100 described in connection with FIG. 1 and/or any other system for applying an application material to an implantable device described herein. For example, the ultrasonic material delivery apparatus 110 and/or the implantable device 180 may have a positive or negative electric charge.

An implantable device may be positioned relative to an ultrasonic material delivery apparatus, as represented by block 202. Positioning an implantable device relative to an ultrasonic material delivery apparatus may include positioning the implantable device in a desired location and/or in a desired orientation. For example, a stent may be positioned about 30 mm from a nozzle of an ultrasonic material delivery apparatus and/or oriented perpendicular to the application material being applied.

In some embodiments, before and/or during the application of the application material to the implantable device, an electric charge may be applied to the ultrasonic material delivery apparatus and/or the implantable device. For example, the system component may be charged before applying the application material, but not during the application of the application material. In this example, the system component may nevertheless be charged by virtue of, for example, retaining the charge. In further embodiments, before applying the application material to the implantable device, the ultrasonic material delivery apparatus and/or the implantable device may be grounded.

An application material may be applied to the implantable device, as represented by block 204. Applying the application material to the implantable device may include moving the implantable device and/or the ultrasonic material delivery apparatus with respect to each other. For example, the ultrasonic material delivery apparatus may move along a length and/or width of the implantable device and the implantable device may rotate to facilitate a generally uniform application of the application material.

Figure 3:
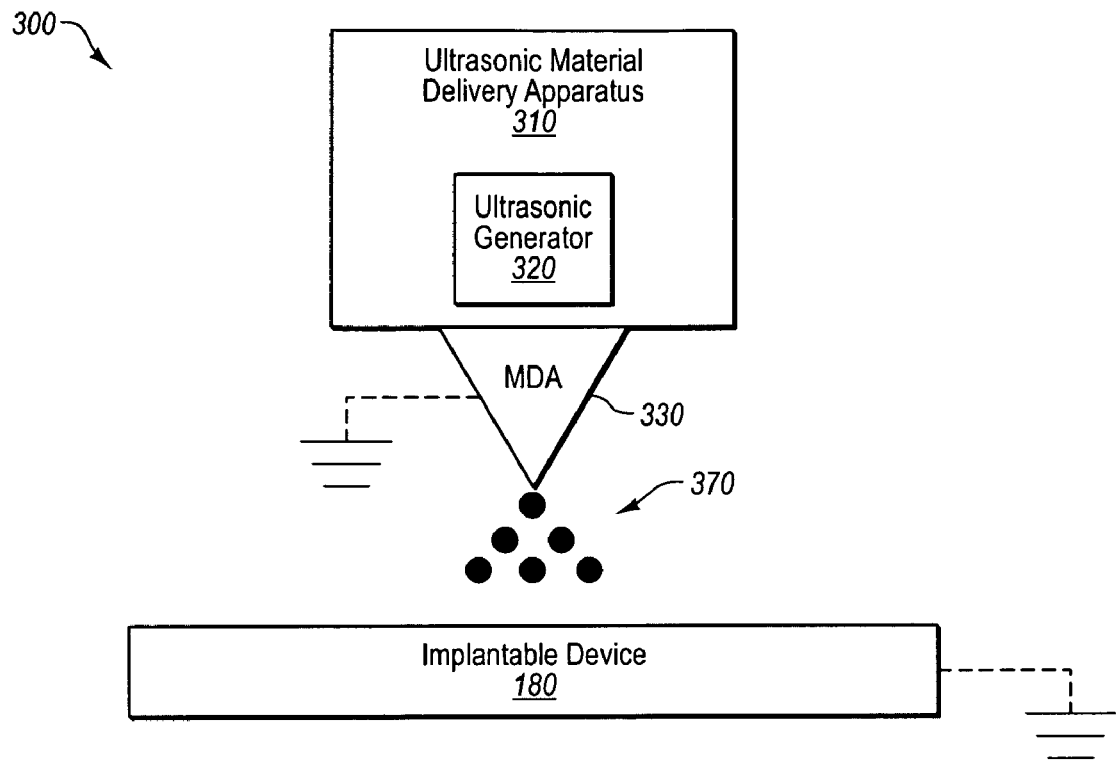
FIG. 3 illustrates a block diagram of another embodiment of a system for applying an application material to an implantable device, in accordance with the present invention.

FIG. 3 illustrates a block diagram of another embodiment of a system 300 for applying an application material 370 to an implantable device 180, in accordance with the present invention. The system 300 of this other embodiment may be functionally similar to that of the system 100 previously described above and shown in FIG. 1 in most respects, wherein certain features will not be described in relation to this other embodiment wherein those components may function in the manner as described above and are hereby incorporated into this alternative embodiment described below.

The system 300 includes an ultrasonic material delivery apparatus 310 that may apply an application material 370 to an implantable device 180. The ultrasonic material delivery apparatus 310, in the present embodiment, may include an ultrasonic generator 320. The ultrasonic generator 320 may include an ultrasonic power generator (not shown) and at least one transducer (not shown, but see description of FIG. 7). The ultrasonic generator 320 may generate ultrasonic energy to facilitate atomization of the application material 370. For example, the ultrasonic generator 320 may generate a transverse standing wave along the length, or at the end of, the nozzle.

The ultrasonic material delivery apparatus 310, in the present embodiment, may include a material delivery apparatus 330. The material delivery apparatus 330 may include, for example, a nozzle body and/or nozzle stem (see, for example, FIG. 7).

The ultrasonic material delivery apparatus 310 and/or the implantable device 180 may have a positive or negative electric charge. The ultrasonic material delivery apparatus 310 or the implantable device 180 may be grounded.

In the present embodiment, the material delivery apparatus 330 may be grounded before and/or during application of the application material. In other embodiments, the material delivery apparatus 330 may have an electric charge before and/or during application of the application material. The material delivery apparatus 330, in the present embodiment, may be selectively electrically isolated from the ultrasonic generator 320. For example, the ultrasonic generator 320 and/or the material delivery apparatus 330 may be electrically insulated.

The implantable device 180 may be grounded, as shown in FIG. 3. However, although the optional ground lines connected to the material delivery apparatus 330 and the implantable device 180 indicate that both may be optionally grounded, only the implantable device 180 or the ultrasonic material delivery apparatus 310 (including the material delivery apparatus 330) may be grounded, in the present embodiment, before and/or during application of the application material 370.

Figure 4:
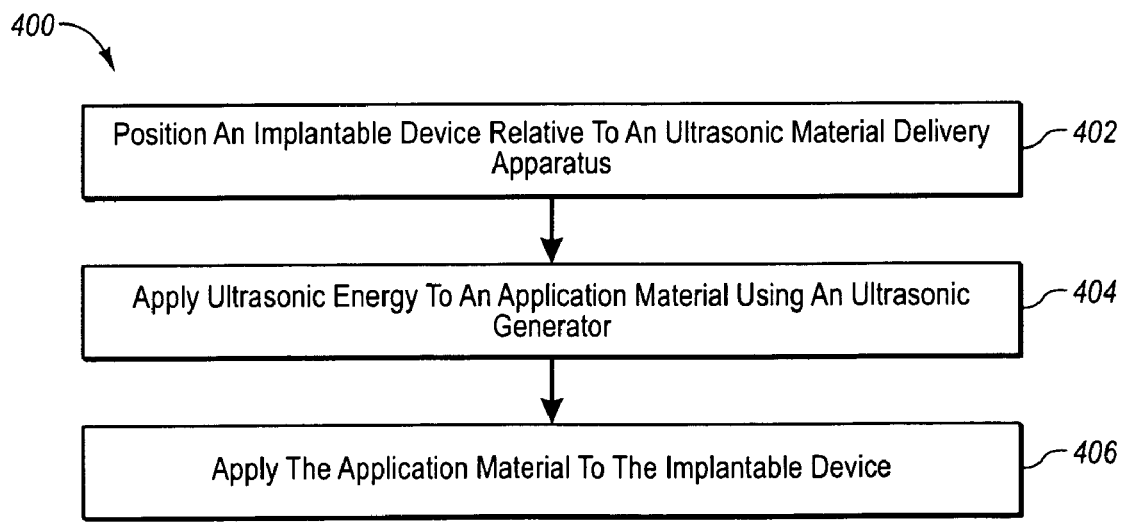
FIG. 4 illustrates another embodiment of a method for applying an application material to an implantable device, in accordance with the present invention.

FIG. 4 illustrates another embodiment of a method 400 for applying an application material to an implantable device, in accordance with the present invention. In the present embodiment, the method 400 may be used in conjunction with components of the systems 100, 300 described in connection with FIGS. 1 and 3 and/or any other system for applying an application material to an implantable device described herein. For example, the method 400 may utilize one of the material delivery apparatus 330 and the implantable device 180.

Figure 2:
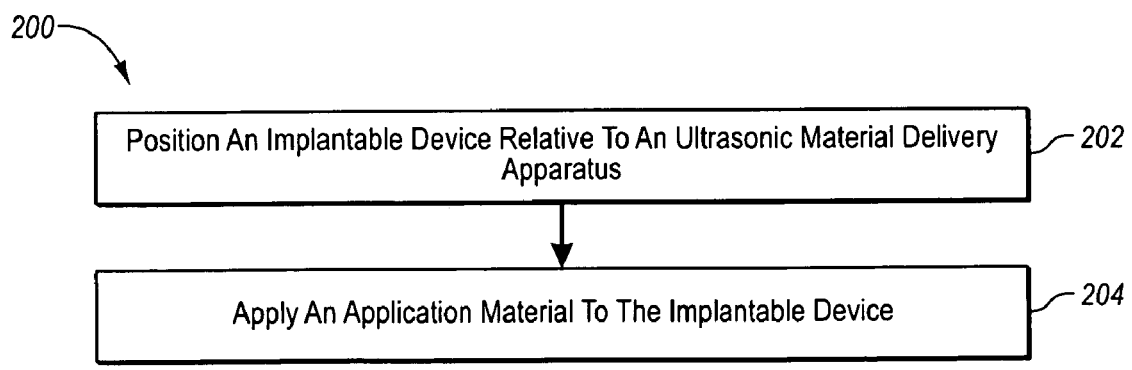
FIG. 2 illustrates an embodiment of a method for applying an application material to an implantable device, in accordance with the present invention.

The method 400 of this other embodiment may be functionally similar to that of the method 200 previously described above and shown in FIG. 2 in most respects, wherein certain features will not be described in relation to this other embodiment wherein those method components may be performed in the manner as described above and are hereby incorporated into this alternative embodiment described below.

An implantable device may be positioned relative to an ultrasonic material delivery apparatus, as represented by block 402. Ultrasonic energy may be applied to an application material using an ultrasonic generator, as represented by block 404. The ultrasonic generator used may include the ultrasonic generator 320 described above. The application material may be applied to the implantable device, as represented by block 406.

Figure 5:
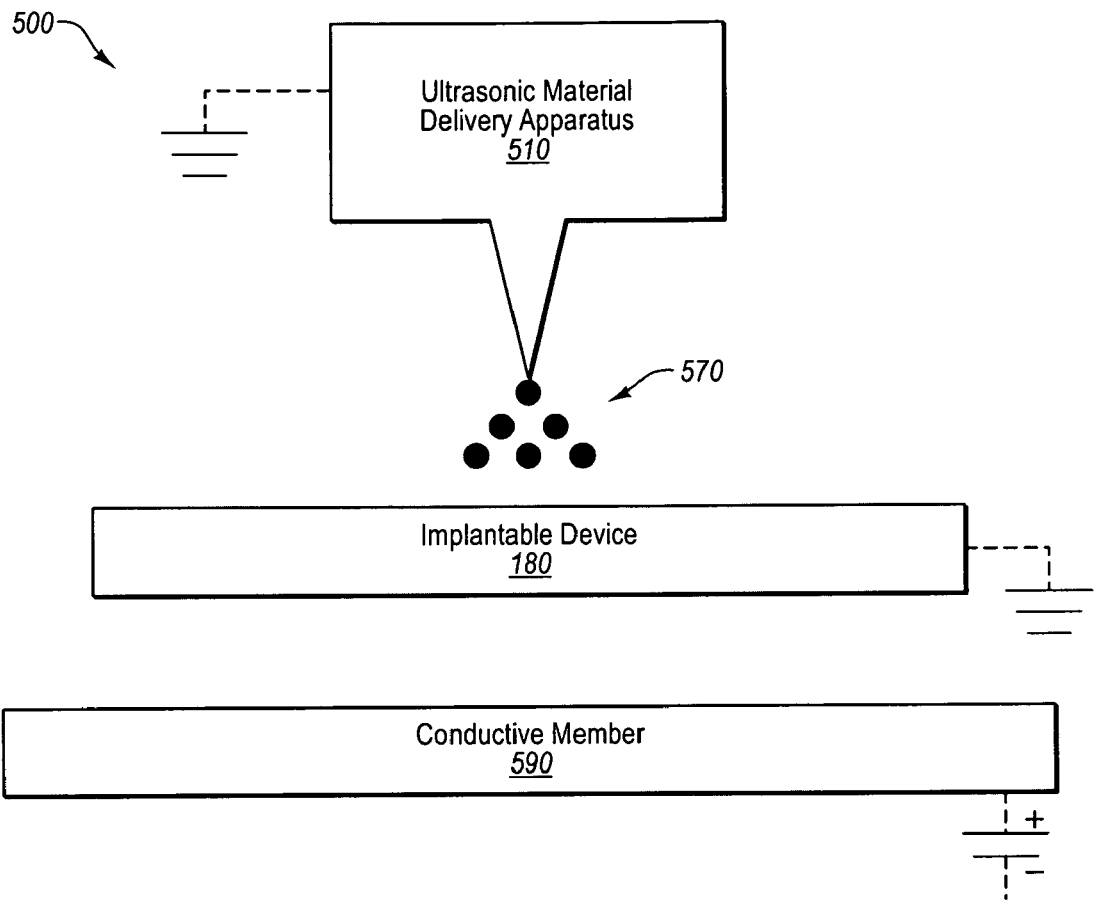
FIG. 5 illustrates a block diagram of a further embodiment of a system for applying an application material to an implantable device, in accordance with the present invention.

FIG. 5 illustrates a block diagram of a further embodiment of a system 500 for applying an application material 570 to an implantable device 180, in accordance with the present invention. The system 500 of this other embodiment may be functionally similar to that of the systems 100, 300 previously described above and shown in FIGS. 1 and 3 in most respects, wherein certain features will not be described in relation to this further embodiment wherein those components may function in the manner as described above and are hereby incorporated into this alternative embodiment described below.

The system 500 includes an ultrasonic material delivery apparatus 510 that may apply an application material 570 to an implantable device 180 and may include a conductive member 590. The ultrasonic material delivery apparatus 510 may include an ultrasonic generator 320 and/or a material delivery apparatus 330.

The conductive member 590 may include an electrically conductive material such as platinum, gold, silver, copper, stainless steel, and/or other electrically conductive materials. As shown in FIG. 5, the conductive member 590 may have an electric charge (shown as positive) applied to it. In the present embodiment, the ultrasonic material delivery apparatus 510, the implantable device 180, the conductive member 590, and/or a combination of the three may have an electric charge, may be grounded, and/or may have an electric charge applied during application of the application material 570. However, at least one of the ultrasonic material delivery apparatus 510, the implantable device 180, and the conductive member 590, in the present embodiment, has an electric charge or has an applied electric charge during application of the application material (i.e., in one configuration no more than two of the ultrasonic material delivery apparatus 510, the implantable device 180, and the conductive member 590 may be grounded during application of the application material).

In embodiments including a conductive member 590, the implantable device 180 may be positioned between the ultrasonic material delivery apparatus 510 and the conductive member 590.

Similar to the previous embodiments, in embodiments where the application material 570, implantable device 180, and/or the conductive member 590 have an electric charge, the application material 570 may be generally attracted to or generally repelled from the implantable device 180 and/or the conductive member 590. In some embodiments, the voltage potential difference between the application material 570 and the implantable device 180 and/or conductive member 590 may be sufficiently large to facilitate atomization of the application material 570.

In systems where the system components include an ultrasonic material delivery device 510, an implantable device 180, and a conductive member 590, various combinations of electrically charged, grounded, and uncharged system components may be used. For example all three system components may have an electric charge (i.e. may have an applied voltage or may retain a previously applied charge), two of the system components may have an electric charge with another system component grounded or uncharged, and/or one system component may have an electric charge with the remaining system components grounded or uncharged. In embodiments where at least two of the system components are electrically charged, the charged system components may all have the same electric charge (i.e. positive or negative) and/or at least one of the charged system components may have a different electric charge than the other charged system components. Furthermore, the charged system components may all have the same quantity of electric charge (i.e. whether positive or negative) or may differ in quantity of electric charge.

In one example, the ultrasonic material delivery apparatus 510 may have a positive electric charge, the implantable device 180 may have a negative electric charge, and the conductive member 590 may have a positive electric charge. When the ultrasonic material delivery apparatus 510 applies the application material 570 to the implantable device 180, the application material 570 may have a positive charge. The positively charged application material 570, in this example, may be generally attracted to the negatively charged implantable device 180 and generally repelled from the positively charged conductive member 590.

The electric charge as well as the quantity of electric charge of the various system components may affect the behavior (i.e. trajectory) of the application material 570. For example, if the ultrasonic material delivery device 510 were grounded during application of the application material 570, the behavior of the application material 570 may be different if the implantable device 180 had an electric charge while the conductive member 590 was grounded compared to the implantable device 180 being grounded while the conductive member 590 had an electric charge. In the example with the charged implantable device 180 and grounded conductive member 590, the application material 570 may have a generally more direct trajectory toward the implantable device 180 than in the example where the implantable device 180 is grounded and the conductive member 590 has an electric charge.

In another example, if the ultrasonic material delivery device 510 were grounded during application of the application material 570 and the conductive member 590 had an electric charge while the implantable device 180 was grounded, the trajectory of the application material 570 may be more direct with respect to the implantable device 180 if the quantity of electric charge of the conductive member 590 were larger than if the quantity of electric charge of the conductive member 590 were smaller. Which system components may have an electric charge or be grounded, the position (i.e. location and/or orientation) of the system components, as well as the quantity of electric charge of the charged system components may be generally selected based on a desired application material 570 trajectory.

Figure 6:
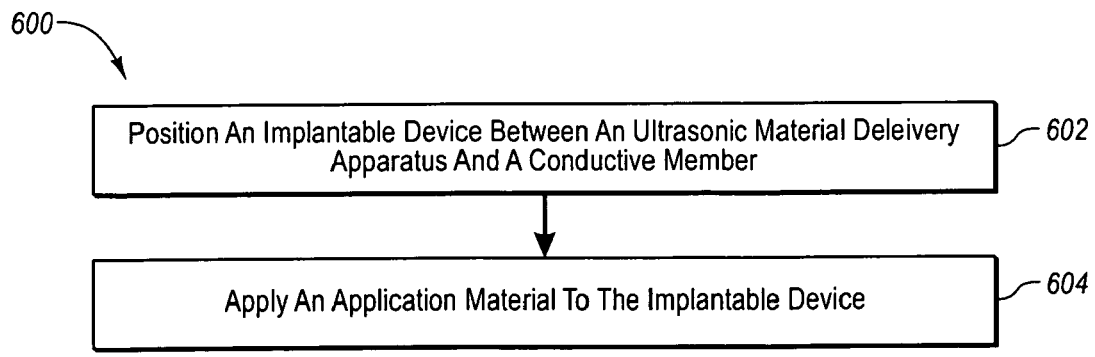
FIG. 6 illustrates a further embodiment of a method for applying an application material to an implantable device, in accordance with the present invention.

FIG. 6 illustrates a further embodiment of a method 600 for applying an application material to an implantable device, in accordance with the present invention. In the present embodiment, the method 600 may be used in conjunction with components of the systems 100, 300, 500 described in connection with FIGS. 1, 3, and 5 and/or any other system for applying an application material to an implantable device described herein. For example, the ultrasonic material delivery apparatus may include an ultrasonic generator 320 and/or a material delivery apparatus 330, which may be selectively electrically isolated from each other.

The method 600 of this further embodiment may be functionally similar to that of the methods 200, 400 previously described above and shown in FIGS. 2 and 4 in most respects, wherein certain features will not be described in relation to this further embodiment wherein those method components may be performed in the manner as described above and are hereby incorporated into this alternative embodiment described below.

An implantable device may be positioned between an ultrasonic material delivery apparatus and a conductive member, as represented by block 602. Positioning an implantable device between an ultrasonic material delivery apparatus and a conductive member may include orienting the implantable device between an ultrasonic material delivery apparatus and a conductive member. For example, a stent may be positioned such that it is about 30 mm from a nozzle of an ultrasonic material delivery apparatus and near the conductive member and/or may be oriented perpendicular to the application material being applied.

In some embodiments, before and/or during application of the application material to the implantable device, an electric charge may be applied to the ultrasonic material delivery apparatus, the implantable device, and/or the conductive member. In further embodiments, before and/or during application of the application material to the implantable device, no more than two of the ultrasonic material delivery apparatus, the implantable device, and conductive member may be grounded.

Application material may then be applied to the implantable device, as represented by block 604.

Figure 7:
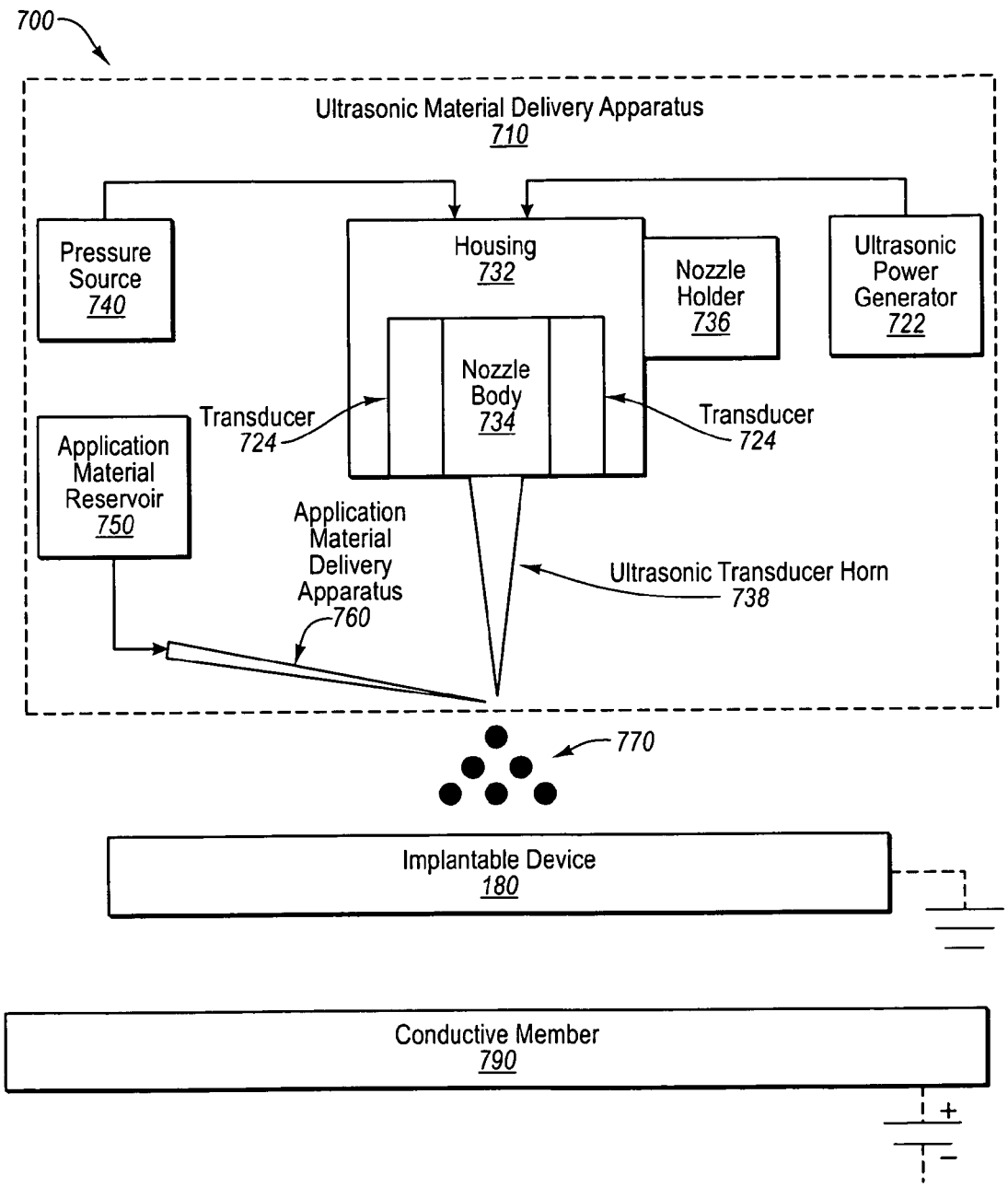
FIG. 7 illustrates a block diagram of a still further embodiment of a system for applying an application material to an implantable device, in accordance with the present invention.

FIG. 7 illustrates a block diagram of a still further embodiment of a system 700 for applying an application material 770 to an implantable device 180, in accordance with the present invention. The system 700 of this still further embodiment may be functionally similar to that of the systems 100, 300, 500 previously described above and shown in FIGS. 1, 3, and 5 in many respects, wherein certain features will not be described in relation to this still further embodiment wherein those components may function in the manner as described above and are hereby incorporated into this alternative embodiment described below.

The system 700 includes an ultrasonic material delivery apparatus 710 that may apply an application material 770 to an implantable device 180 and may include a conductive member 790. The ultrasonic material delivery apparatus 710, in the present embodiment, may include an ultrasonic power generator 722, a transducer 724, a housing 732, a nozzle body 734, a nozzle holder 736, an ultrasonic transducer horn 738, a pressure source 740, an application material reservoir 750, and/or an application material delivery apparatus 760.

The system 700, in the present embodiment, may include an ultrasonic generator. The ultrasonic generator may include an ultrasonic power generator 722 and at least one transducer 724. The ultrasonic power generator 722 may generate high frequency electrical energy. High frequency electrical energy may be generated in the range, for example, from about 20 kHz to about 120 kHz. The frequency may be determined based on the characteristics of the nozzle body 734 and/or ultrasonic horn 738.

The ultrasonic power generator 722 may be in electrical communication with at least one transducer 724. The at least one transducer 724 may convert the electrical energy generated by the ultrasonic power generator 722 into mechanical (i.e. vibration) energy. The transducers 724 may include piezoelectric transducers to facilitate in atomizing the application material 770.

The housing 732 may house the nozzle body 734. The housing 732 may be connected to the nozzle holder 736. The nozzle holder 736 may be used to position the ultrasonic material delivery apparatus 710 with respect to the implantable device 180 and/or conductive member 790.

In the present embodiment, the material delivery apparatus (not shown) may include both an application material delivery apparatus 760 and a nozzle body 734 and ultrasonic horn 738. In other embodiments, other configurations may be used. For example, the nozzle body 734 and ultrasonic horn 738 may be in fluid communication with the application material reservoir 750 and a pressure source 740.

The nozzle body 734 and/or the ultrasonic horn 738, in the present embodiment, may be in fluid communication with a pressure source 740. The pressure source 740, in the present embodiment, may include an air pressure source. The pressure source 740 may generate a pressurized fluid that may be shaped and/or directed by the nozzle body 734 and/or the ultrasonic horn 738. The pressure source 740, in the present embodiment, may generate a low-pressure air stream. In one embodiment, ultrasonic horn 738 may be hollow with the gas from pressure source 740 passing through it.

The application material delivery apparatus 760 may be connected to an application material reservoir 750. The application material reservoir 750 may include a pump, pressurized reservoir, gravity system, and/or other delivery mechanism to direct the application material 770 to the application material delivery apparatus 760. The application material delivery apparatus 760 may include a hypotube. The application material delivery apparatus 760 may deliver the application material 770 to the ultrasonic horn 738 to facilitate atomization of the application material 770. In some embodiments, the application material delivery apparatus 760 may have an electric charge and/or be grounded. In further embodiments, the application material delivery apparatus 760 may be selectively electrically isolated from the ultrasonic power generator 722.

As in the previous embodiments, which system components may have an electric charge or be grounded as well as the quantity of electric charge of the charged system components may be generally selected based on a desired application material 770 trajectory.

Figure 8:
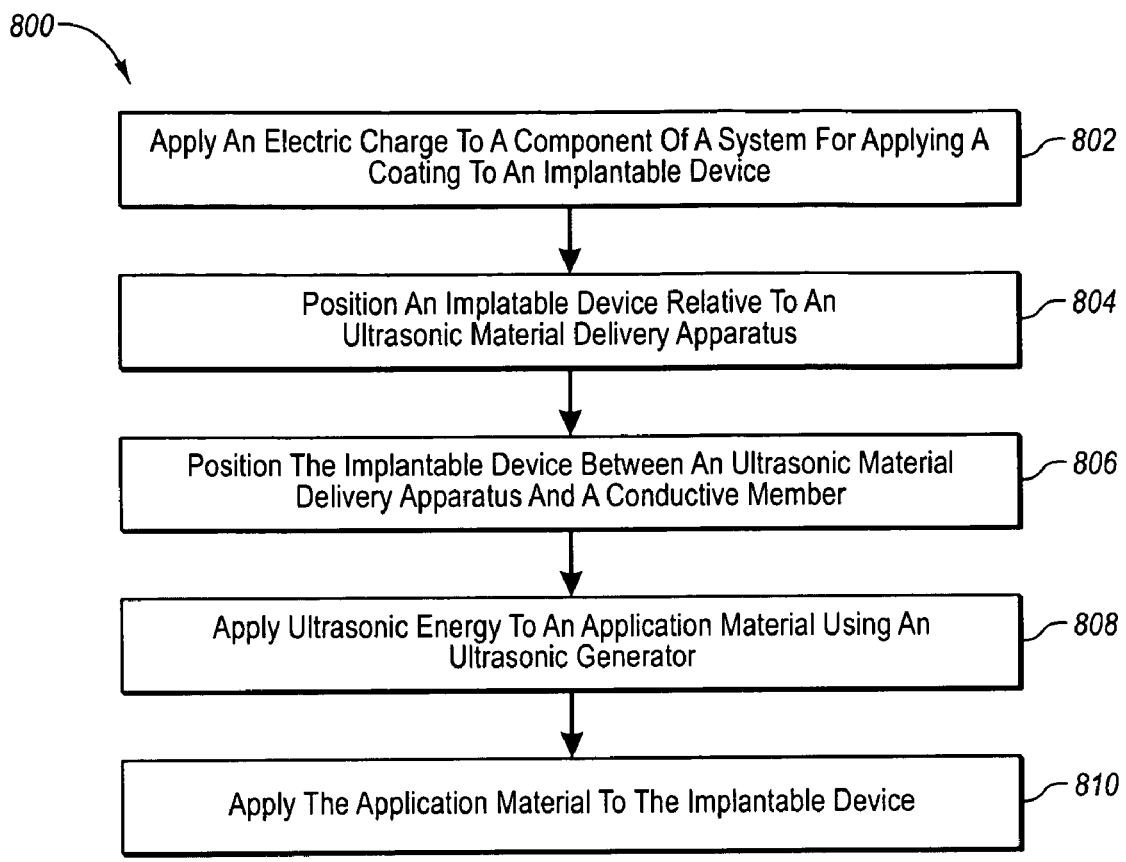
FIG. 8 illustrates a still further embodiment of a method for applying an application material to an implantable device, in accordance with the present invention.

FIG. 8 illustrates a still further embodiment of a method 800 for applying an application material to an implantable device, in accordance with the present invention. The method 800 may utilize systems for applying a coating to an implantable device such as the systems 100, 300, 500, 700 previously described above and shown in FIGS. 1, 3, 5, and 7. Components of these systems 100, 300, 500, 700 may include an ultrasonic material delivery apparatus 110 (or components of an ultrasonic material delivery apparatus 310 or 710 such as an application material delivery apparatus 760, a transducer 724, an ultrasonic power generator 722, and/or other system components), an implantable device 180, and/or a conductive member 590.

The method 800 of this still further embodiment may be functionally similar to that of the methods 200, 400, 600 previously described above and shown in FIGS. 2, 4, and 6 in most respects, wherein certain features will not be described in relation to this still further embodiment wherein those method components may be performed in the manner as described above and are hereby incorporated into this alternative embodiment described below.

An electric charge may be applied to a component of a system for applying a coating to an implantable device, as represented by block 802. The electric charge applied to a component of a system for applying a coating to an implantable device may be applied before and/or maintained during application of the application material. For example, an electric charge may be applied to an application material delivery apparatus during application of the application material.

The implantable device may be positioned relative to an ultrasonic material delivery apparatus, as represented by block 804. The implantable device may be positioned between the ultrasonic material delivery apparatus and a conductive member, as represented by block 806. Ultrasonic energy may be applied to an application material using an ultrasonic generator, as represented by block 808. Application material may be applied to the implantable device, as represented by block 810.

Figure 9:
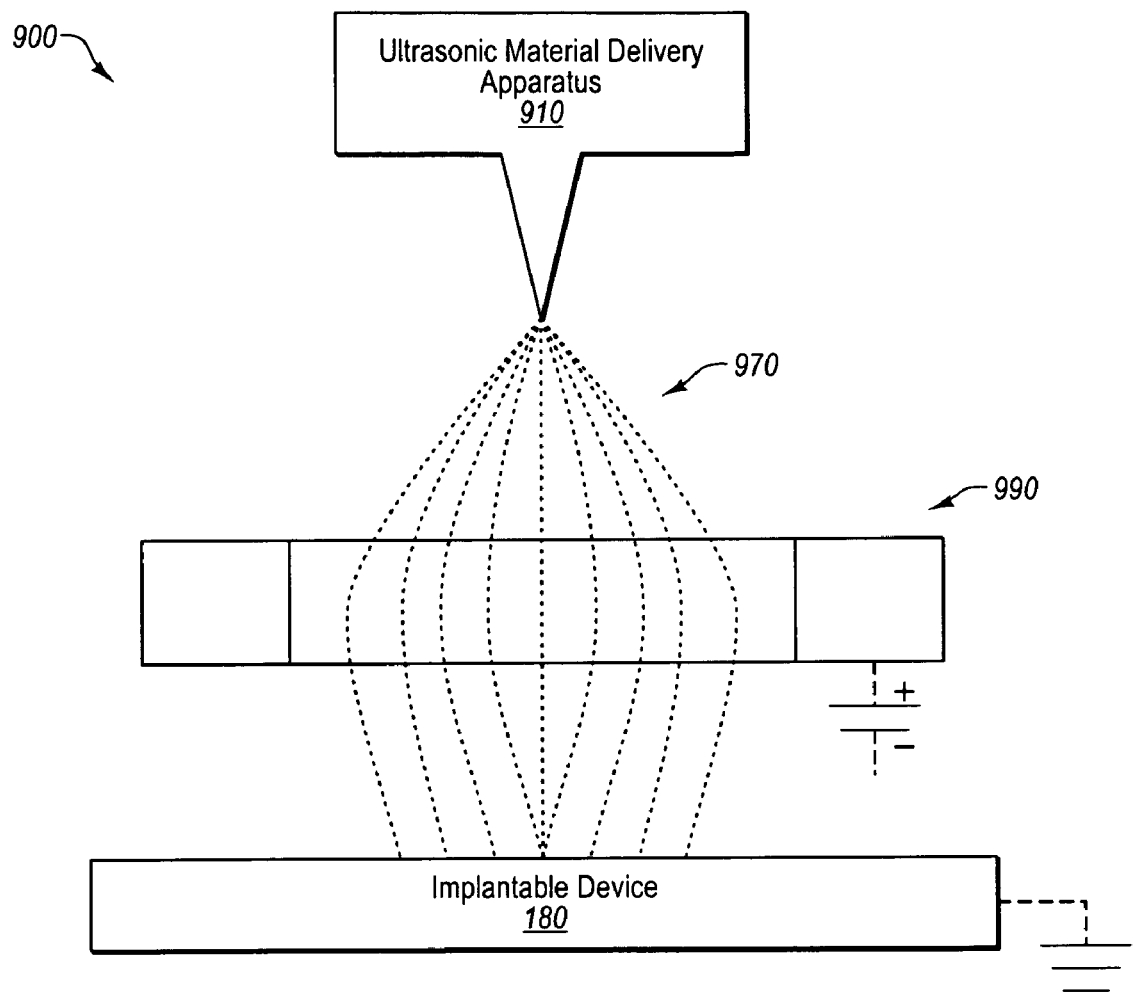
FIG. 9 illustrates a block diagram of an even further embodiment of a system for applying an application material to an implantable device, in accordance with the present invention.

FIG. 9 illustrates a block diagram of an even further embodiment of a system 900 for applying an application material 970 to an implantable device 180, in accordance with the present invention. The system 900 of this embodiment may be functionally similar to that of systems 100, 300, 500, 700 previously described above and shown in FIGS. 1, 3, 5, and 7 in many respects. As such, certain features will not be described in relation to this embodiment wherein those components may function in the manner as described above and are hereby incorporated into this alternative embodiment described below. Like structures or components are give like reference numerals.

The system 900 includes an ultrasonic material delivery apparatus 910 that may apply an application material 970 to an implantable device 180 and may include a conductive member 990. The ultrasonic material delivery apparatus 910 may include an ultrasonic generator 320 and/or a material delivery apparatus 330.

The conductive member 990 may include an electrically conductive material such as platinum, gold, silver, copper, stainless steel, and/or other electrically conductive materials. As shown in FIG. 9, the conductive member 990 may have an electric charge (shown as positive) applied to it. The ultrasonic material delivery apparatus 910, the implantable device 180, the conductive member 990, and/or a combination of the three may have an electric charge, may be grounded, and/or may have an electric charge applied during application of the application material 970. However, at least one of the ultrasonic material delivery apparatus 910, the implantable device 180, and the conductive member 990, in the present embodiment, has an electric charge or has an applied electric charge during application of the application material (i.e., in one configuration no more than two of the ultrasonic material delivery apparatus 910, the implantable device 180, and the conductive member 990 may be grounded during application of the application material).

Similar to the previous embodiments, in embodiments where the application material 970, implantable device 180, and/or the conductive member 990 have an electric charge, the application material 970 may be generally attracted to or generally repelled from the implantable device 180 and/or the conductive member 990. In some embodiments, the voltage potential difference between the application material 970 and the implantable device 180 and/or conductive member 990 may be sufficiently large to facilitate atomization of the application material 970.

In the present embodiment, the conductive member 990 may be positioned between the ultrasonic material delivery apparatus 910 and the implantable device 180. In other embodiments, the ultrasonic material delivery apparatus 910, the conductive member, and/or the implantable device 180 may be otherwise positioned.

The conductive member 990 is illustrated in FIG. 9 as an annular ring. In other embodiments, the conductive member 990 may be tubular, cylindrical, spherical, rectangular, and/or otherwise shaped to perform the desired function of aiding to direct the flow of application material to the implantable device.

The conductive member 990 may perform additional functions. For example, the conductive member 990 may include a focusing assembly that uses a deflecting fluid to focus the trajectory of the application material 970. Deflecting a fluid path using a focusing assembly may be accomplished as disclosed in U.S. Patent Application No. 61/015,137, filed Dec. 19, 2007, and entitled "METHODS FOR APPLYING AN APPLICATION MATERIAL TO AN IMPLANTABLE DEVICE", which is incorporated herein by reference in its entirety. For example, the conductive member 990 may include an annular focusing jet to deflect the trajectory of the application material 970.

As in the previous embodiments, which system components may have an electric charge or be grounded as well as the magnitude of electric charge of the charged system components may be generally selected based on a desired application material 970 trajectory.

Figure 10:
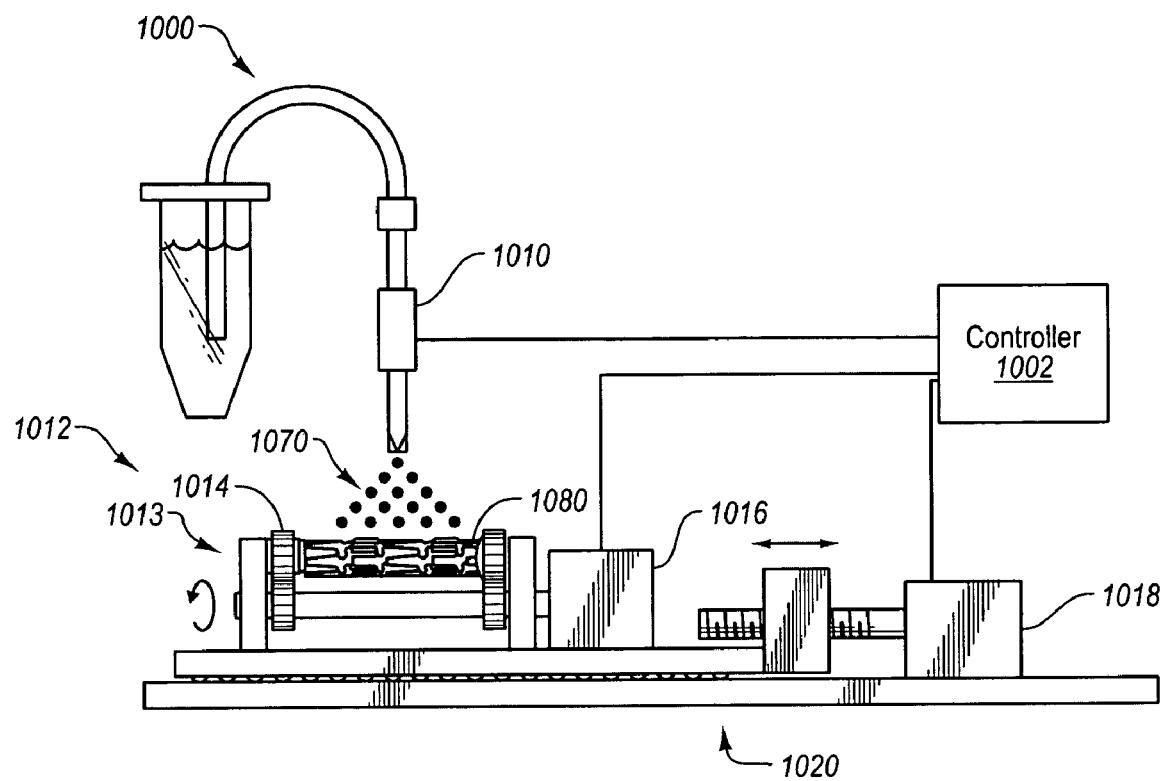
FIG. 10 illustrates a schematic representation of an embodiment of a system for applying an application material to an implantable device, in accordance with the present invention.

FIG. 10 illustrates a schematic representation of an embodiment of a system 1000 for applying an application material 1070 to an implantable device 1080, in accordance with the present invention. The system 1000 of this embodiment may be functionally similar to that of systems 100, 300, 500, 700, 900 previously described above and shown in FIGS. 1, 3, 5, 7, and 9 in many respects, wherein certain features will not be described in relation to this embodiment wherein those components may function in the manner as described above and are hereby incorporated into this alternative embodiment described below. Like structures or components are give like reference numerals.

The system 1000 may include an ultrasonic material delivery apparatus 1010 that may apply an application material 1070 to an implantable device 1080. The delivery or loading of the application material 1070 to the implantable device 1080 can be varied through use of a controller 1002, the ultrasonic material delivery apparatus 1010, a positioning assembly 1012, and/or other components. For instance, the controller 1002 can be programmed with the structural configuration of the implantable device 1080 and control delivery or loading the application material 1070 through controlling the operation of the ultrasonic material delivery apparatus 1010, the positioning assembly 1012, and/or other components. Other components may include a focusing assembly that may deflect or change a spray pattern of the application material 1070. In this manner, the invention reduces or eliminates webbing and bridging of application material across openings or gaps within the structure of the prosthesis and minimizes waste.

The positioning assembly 1012 can include a driver assembly 1020 that creates relative movement between the implantable device 1080 and the ultrasonic material delivery apparatus 1010. The positioning assembly 1012 can also include a rotation assembly 1013 that creates rotational movement of the implantable device 1080 and/or a holder 1014 configured to support and/or rotate the implantable device 1080.

As mentioned above, the controller 1002 in communication with the driver assembly 1020 can define a dispensing path of relative movement between the ultrasonic material delivery apparatus 1010 and the rotation assembly 1013. The controller 1002 can also communicate with the ultrasonic material delivery apparatus 1010 for selectively dispensing application material 1070 in a selected format along the dispensing path onto a selected portion of the implantable device 1080 supported by the holder 1014. In one configuration, the rotation assembly 1013 supporting the implantable device 1080 is longitudinally moveable while the ultrasonic material delivery apparatus 1010 remains stationary during dispensing of application material 1070. However, in another aspect of the invention the rotation assembly 1013 supporting the implantable device 1080 may remain longitudinally stationary (although may still rotate) while the ultrasonic material delivery apparatus 1010 moves along the dispensing path. Alternatively, both the rotation assembly 1013 and ultrasonic material delivery apparatus 1010 are longitudinally moveable.

In another configuration, the system 1000 can include a detector or sensor to detect when the ultrasonic material delivery apparatus 1010 is aligned with the selected portions of the implantable device 1080. Such a detector or sensor can be an optical detector, e.g., linear array detector or infrared detector, ultrasound probe, temperature probe, camera, capacitance meter, electrometer, hall-effect probe, and the like, or any other sensor or detector known in the art for detection.

In a further configuration, the system 1000 can include a focusing assembly to aid delivery or loading application material 1070 through varying or changing the spray pattern of the application material 1070. The focusing assembly may include at least one focusing jet, an annular jet, and/or other focusing assembly components.

With continued reference to FIG. 10, the positioning assembly 1012 can further include a longitudinal driver 1018. The rotation assembly 1013 can likewise further include a rotating driver 1016. The holder 1014 may be rotated through the rotation driver 1016, which can include a motor. For instance, the rotating driver 1016 can be activated to produce a constant angular velocity on the implantable device 1080 during application material delivery. Similarly, the longitudinal driver 1018 can control advancement of the implantable device 1080 longitudinally past the ultrasonic material delivery apparatus 1010. Again, the longitudinal driver 1018 can include a motor.

Through the system 1000, application material 1070 can be loaded or delivered to an implantable device 1080 in a controlled manner. The system 1000 enables and facilitates relative movement between the material application apparatus 1010 and the implantable device 1080 to define a dispensing path along which the application material 1070 can be selectively dispensed. The positioning assembly 1012 and/or rotation assembly 1013 may aid the delivery or loading of the application material 1070 through varying or changing the spray pattern of the application material 1070. Hence, the application material 1070 is selectively dispensed from the ultrasonic material delivery apparatus 1010 to a predetermined portion of the implantable device 1080 along the dispensing path.

The dispensing path can include, for example, a sequential series of linear parallel passes that traverse back and forth along one axis of the implantable device 1080. The relative motion can be continued in a linear manner between forward and backward or right to left and left to right or upward and downward, depending on the frame of reference. A traversal or a pass can be completed when the relative motion reverses direction. That is, relative motion continues past the implantable device, and then decelerates, stops, reverses direction, and/or accelerates to a constant velocity. After each pass, the system 1000 may adjust the position of the ultrasonic material delivery apparatus 1010 and/or implantable device 1080 relative to the ultrasonic material delivery apparatus 1010 can be changed or incremented to limit the possibility of application overlap, although a certain degree of overlap may be permitted.

Alternatively, the dispensing path created by the relative motion of the ultrasonic material delivery apparatus 1010 and the implantable device 1080 can include a single continuous helix that wraps continuously around the implantable device tubular body and along the length of the implantable device 1080. Alternatively, the dispensing path can include a non-continuous helix.

The invention is susceptible to various modifications and alternative means, and specific examples thereof have been shown by way of example in the drawings and are herein described in detail. It should be understood, however, that the invention is not to be limited to the particular devices or methods disclosed, but to the contrary, the invention is to cover all modifications, equivalents, and alternatives falling within the spirit and scope of the claims.

What is claimed is:

1. A method for applying a coating to an implantable device, comprising:
    positioning an implantable device relative to an ultrasonic material delivery apparatus, the ultrasonic material delivery apparatus being configured to deliver a liquid application material to the implantable device, the ultrasonic material delivery apparatus including an ultrasonic generator, a nozzle body, and an ultrasonic horn;
    applying a charge to both the implantable device and the liquid application material, the implantable device having a charge opposite to that of the application material; and
    applying the liquid application material to the implantable device using the ultrasonic material delivery apparatus to coat the implantable device.

2. The method of claim 1, further comprising during application of the material to the implantable device applying a voltage potential to the ultrasonic material delivery apparatus to give the ultrasonic material delivery apparatus one of: a positive electric charge or negative electric charge.

3. The method of claim 2, wherein the material delivery device is selectively electrically isolated from the ultrasonic generator.

4. The method of claim 2, wherein the material delivery apparatus combines ultrasonic atomization with a flowing gas stream.

5. The method of claim 1, wherein the ultrasonic material delivery apparatus has a positive or negative electric charge and the positive or negative electric charge is of sufficient strength to assist with atomization of the application material.

6. The method of claim 1, further comprising positioning the implantable device between the ultrasonic material delivery apparatus and a conductive member.

7. The method of claim 6, wherein the conductive member either has a positive or a negative charge or is grounded.

8. The method of claim 1, further comprising positioning a conductive member between the implantable device and the ultrasonic material delivery apparatus.

9. The method of claim 8, wherein the conductive member either has a positive or a negative charge or is grounded.

10. The method of claim 1, wherein the implantable device, the ultrasonic material delivery apparatus, or the conductive member have a difference in electrical potential of less than or equal to about 100 kV in either a positive or negative polarity.

11. The method of claim 1, wherein both the implantable device and the ultrasonic material delivery apparatus have either a positive or a negative charge.

12. The method of claim 1, wherein the application material includes a radiopaque material.

13. The method of claim 1, wherein the application material includes at least one bioactive agent that is an anti-proliferative, anti-inflammatory, antineoplastic, antiplatelet, anti-coagulant, anti-fibrin, antithrombonic, antimitotic, antibiotic, antiallergic or antioxidant drug.

14. The method of claim 1, wherein the application material includes a durable or biodegradable polymer.

15. The method of claim 1, wherein the application material includes a solvent.

16. The method of claim 1, wherein the implantable device is a closure element.

17. The method of claim 1, wherein the implantable device is a stent.

18. The method of claim 2, further comprising at least one of the material delivery device and the implantable device being grounded.

19. A method for applying a coating to an implantable device, the method comprising:
    positioning an implantable device between a conductive member and an ultrasonic material delivery apparatus, the ultrasonic material delivery apparatus being configured to deliver a liquid application material to the implantable device, the ultrasonic material delivery apparatus including an ultrasonic generator, a nozzle body, and an ultrasonic horn and the conductive member either having a positive or a negative charge; and
    applying a charge to the liquid application material, the conductive member having a charge opposite to that of the liquid application material; and
    applying the liquid application material to the implantable device using the ultrasonic material delivery apparatus to coat the implantable device.

20. The method of claim 19, further comprising at least one of the ultrasonic material delivery apparatus and the implantable device being grounded.

21. The method of claim 19, wherein the application material includes a radiopaque material.

22. The method of claim 19, wherein the application material includes at least one bioactive agent that is an anti-proliferative, anti-inflammatory, antineoplastic, antiplatelet, anti-coagulant, anti-fibrin, antithrombonic, antimitotic, antibiotic, antiallergic or antioxidant drug.

23. A method for applying a coating to a stent, the method comprising:

positioning a stent between an ultrasonic material delivery apparatus and a grounded conductive member, the ultrasonic material delivery apparatus being configured to deliver a liquid application material to the implantable device, the ultrasonic material delivery apparatus including an ultrasonic generator, a nozzle body, and an ultrasonic horn, at least one of the ultrasonic material delivery apparatus and the stent having a positive or negative electric charge;

applying ultrasonic energy to an application material using the ultrasonic generator;

applying a charge to both the stent and the liquid application material, the stent having a charge opposite to that of the liquid application material; and applying the liquid application material to the stent using the ultrasonic material delivery apparatus to coat the stent.

24. The method of claim 23, wherein the applied ultrasonic energy is sufficient to facilitate atomization of the application material.

25. The method of claim 23, wherein the stent has a positive or negative electric charge and the positive or negative electric charge is of sufficient strength to facilitate atomization of the application material.

26. A method for applying a coating to an implantable device, the method comprising:

positioning a conductive member between an implantable device and an ultrasonic material delivery apparatus, the ultrasonic material delivery apparatus being configured to deliver a liquid application material to the implantable device, the ultrasonic material delivery apparatus including an ultrasonic generator, a nozzle body, and an ultrasonic horn, and the conductive member either having a positive or a negative charge; and applying a charge to the liquid application material, the conductive member having a charge opposite to that of the liquid application material; and applying the application material to the implantable device using the ultrasonic material delivery apparatus to coat the implantable device.

27. The method of claim 26, further comprising at least one of the ultrasonic material delivery apparatus and the implantable device being grounded.

28. The method of claim 26, wherein the application material includes a radiopaque material.

29. The method of claim 26, wherein the application material includes at least one bioactive agent that is an anti-proliferative, anti-inflammatory, antineoplastic, antiplatelet, anti-coagulant, anti-fibrin, antithrombonic, antimitotic, antibiotic, antiallergic or antioxidant drug.

* * * * *